United States Patent [19]

Kato et al.

[11] Patent Number: 5,320,735
[45] Date of Patent: Jun. 14, 1994

[54] ELECTRODE FOR MEASURING PH

[75] Inventors: Akihiko Kato; Masaharu Yamasato; Tomio Taguchi; Yoshiki Yanagida, all of Saitama; Teruaki Katube, Tokyo, all of Japan

[73] Assignee: Toa Electronics Ltd., Tokyo, Japan

[21] Appl. No.: 747,885

[22] Filed: Aug. 19, 1991

[30] Foreign Application Priority Data

| Aug. 22, 1990 | [JP] | Japan | 2-220733 |
| Aug. 22, 1990 | [JP] | Japan | 2-220861 |
| Jul. 30, 1991 | [JP] | Japan | 3-214523 |

[51] Int. Cl.$^5$ ......................................... G01N 27/333
[52] U.S. Cl. ............................. 204/419; 204/153.21; 204/192.1; 204/192.11; 204/416; 204/433; 204/435
[58] Field of Search ................ 204/153.21, 416, 418, 204/419, 420, 435, 433

[56] References Cited

U.S. PATENT DOCUMENTS

| 2,882,213 | 4/1959 | Douglas | 204/197 |
| 3,726,777 | 4/1973 | Macur | 204/433 |
| 3,954,590 | 5/1976 | Czuha | 204/430 |
| 4,020,830 | 5/1977 | Johnson et al. | 204/412 |
| 4,052,285 | 10/1977 | Dobson | 204/418 |
| 4,133,735 | 1/1979 | Afromowitz et al. | 204/420 |
| 4,218,298 | 8/1980 | Shimada et al. | 204/418 |
| 4,280,889 | 7/1981 | Szonnzagh | 204/420 |
| 4,305,802 | 12/1981 | Koshiishi | 204/418 |
| 4,402,820 | 9/1983 | Sano et al. | 204/429 |
| 4,885,077 | 12/1989 | Karakelle et al. | 204/403 |
| 5,110,441 | 5/1992 | Kinlen et al. | 204/433 |

FOREIGN PATENT DOCUMENTS

| 1219632 | 3/1987 | Canada . | |
| 0125560 | 11/1984 | European Pat. Off. . | |
| 0277472 | 8/1988 | European Pat. Off. . | |
| 282349 | 9/1988 | European Pat. Off. | 204/416 |
| 0433261 | 6/1991 | European Pat. Off. . | |
| 59-151053 | 12/1984 | Japan . | |

OTHER PUBLICATIONS

"Palladium-Palladium Oxide pH Electrodes", Anal. Chem., vol. 52, pp. 270-273 (1980).
"High Temperature and High Pressure pH Sensors with Sputtered Iridium Oxide Films", Japanese Journal of Applied Physics, vol. 22, pp. 469-472 (1983).
Search Report dated Nov. 29, 1991 in European Patent Application No. 91307647.
"pH-Sensitive Sputtered Iridium Oxide Film", Sensors and Actuators, 2, (1982), pp. 399-410.
"Electronic Semiconducting Oxides as pH Sensors", Sensors and Actuators, 5, (1984), pp. 137-146.
"Instability in pH Measurements of Sputtered IrO$_2$ Films", Kreider et al., Transducers '87, pp. 734-737 (1987).
"pH Dependent Voltammetry of Iridium Oxide Films", Yuen et al. believed to have been published in Solid State Ionics, 11, pp. 19-29 (1983).
"Electrically Free-Standing IrO$_x$ Thin Film Electrodes for High Temperature, Corrosive Environment pH Sensing", Sensors and Actuators, 4 (1983), pp. 375-379.
"Mechanistic and Response Studies of Iridium Oxide pH Sensors", Sensors and Actuators, B1 (1990), pp. 293-297.
"pH Sensor Properties of Electrochemically Grown Iridium Oxide", Sensors and Actuators, B2 (1990), pp. 247-256.
"Metal-Metal Oxide and Metal Oxide Electrodes as pH Sensors", Analytical Chemistry, 21, (1989), pp. 29-47.
"Evaluation of Iridium Oxide Electrodes Formed by Potential Cycling as pH Probes", Analyst, 113, (1988), pp. 35-39.

Primary Examiner—T. Tung
Attorney, Agent, or Firm—Panitch Schwarze Jacobs & Nadel

[57] ABSTRACT

This invention relates to a pH measuring electrode having a sensor film which is sensitive to a hydrogen ion (H+) in the solution and method of manufacturing the same. The pH measuring electrode of this invention has a sensor film of a metal oxide deposited on an electrically conductive support so that the sensor film can be very miniaturized in its size. Therefore, the entire pH measuring electrode can be made considerably small and simple in construction. Also, this invention provides another pH measuring electrode which further includes a porous film of an insulation material coated on the surface of the metal oxide sensor film so that the sensor film is not affected by any coexistent substances.

10 Claims, 5 Drawing Sheets

F I G. 1
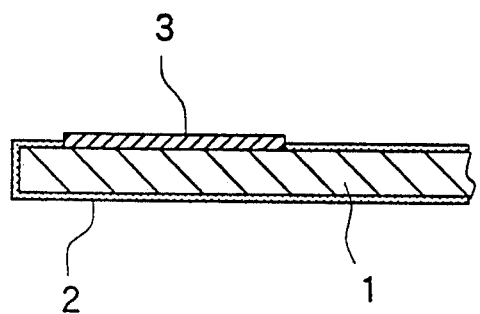
F I G. 2
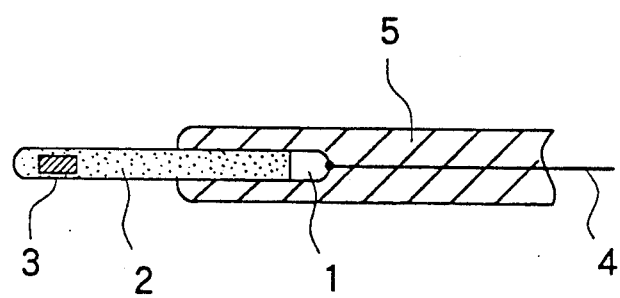

ELECTRODE FOR MEASURING PH

BACKGROUND OF THE INVENTION

1. Field of the Invention

The present invention relates to a pH measuring electrode for use in measuring the pH of a solution and a method of manufacturing the same. More particularly, it relates to a pH measuring electrode in which a metal oxide is used as a sensitive film (sensor film) thereof and a method of manufacturing the same.

2. Description of the Related Art

As is well known, to measure the pH of a solution, a pH measuring electrode having a sensor film which is sensitive to a hydrogen ion (H+) in the solution is used. A typical example of such an electrode is a glass electrode in which the glass is employed as a sensor membrane. Recently, ISFET electrodes have also come to be used in a limited scope of fields. Furthermore, for a special solution, such as a high temperature solution or the like, or for a special application, a pH measuring electrode in which a metal such as platinum or the like, or a metal oxide such as titanium oxide or the like is employed as a sensitive film thereof, is used.

When pH of a solution is actually measured, said pH measuring electrode is used as a working electrode and is immersed in a solution to be measured together with a reference electrode such as a calomel electrode, silver-silver chloride electrode or the like, and a pH value of the solution to be measured is determined from the electric potential difference between both the electrodes.

Since glass electrodes are quite stable and are capable of making highly accurate measurements, they are greatly used to measure the pH of various kinds of solutions. However, glass electrodes are liable to be easily broken, and therefore they are troublesome to handle. Further, because they have poor resistance to chemicals, there is a limitation in the number of solutions pH of which can be measured by the glass electrodes. In addition, there is a problem in that, since an electric resistance value of the glass membrane is high, glass electrodes are difficult to miniaturize from the viewpoint of current manufacturing technology, which is a serious disadvantage as there is an increased demand for the miniaturization of pH meters and other pH measuring instruments.

For this reason, various types of electrodes for measuring pH which are capable of eliminating these drawbacks have been investigated, and the pH measuring electrodes in which the above-mentioned metals or metal oxides are used as sensitive films thereof, or ISFET electrode, have been provided.

However, the above-described conventional pH measuring electrodes in which metals or metal oxides are employed as sensitive films thereof have problems in that the range of pH the electrodes can measure is quite limited depending upon the kind of sensitive film employed therein, and that for a short period of time, stable measurements of pH cannot be made. For example, if there is a coexistent substance such as an oxidizing agent or a reducing agent in a solution to be measured, a great drift in electric potential measured by the electrode is caused and an accurate pH measurement could not be made. Also, ISFET electrodes have such problems that their drifts are great, that they are affected by light, that special amplifying circuits are required, etc.

The inventors have confirmed, after various kinds of experiments have been carried out, that to use iridium oxide as a sensitive film of a pH measuring electrode is effective. Well-known thin-film production technology such as sputtering, ion-beam deposition, ion plating or CVD, was used to form an iridium oxide film on an insulation substrate. However, in case that an iridium oxide film was formed on an insulation substrate, there is a limitation in the shape of the substrate. Also, since it is required to cover the lead-out portion of a lead wire secured to the iridium oxide film with a bonding agent, its workability is poor. In addition, it is difficult to make such electrode small at will.

SUMMARY OF THE INVENTION

Accordingly, an object of the present invention is to provide a pH measuring electrode in which a metal oxide is employed as a sensitive film thereof, which is capable of making an pH measurement with an accuracy comparable to that of a glass electrode without being influenced by any coexistent substance.

Another object of the present invention is to provide a method of producing a pH measuring electrode in which a metal oxide is employed as a sensor film thereof, which is capable of forming the whole electrode in very small size and in any shape with excellent workability.

A further object of the present invention is to provide a method of producing a pH measuring electrode in which a metal oxide is employed as a sensitive film, said electrode produced thereby being durable, having high resistance to chemicals, being able to measure pH of a solution over a wide range, and being capable of making stable measurements for a long period of time.

The above-described objects can be achieved by a pH measuring electrode and a method of manufacturing the same according to the present invention. In summary, in one aspect of this invention, a pH measuring electrode is provided, which comprises an electrically conductive support body, an insulation film formed on the surface of said support body with a portion thereof remaining exposed, and a sensor film of a metal oxide formed at least on said exposed portion of the support body.

In another aspect of this invention, a pH measuring electrode of the present invention has a porous film of an insulation material deposited on the entire surface of a sensor film of a metal oxide at least at the portion thereof where the metal oxide contact with a solution pH of which is measured.

In further aspect of this invention, a method of producing a pH measuring electrode is provided, which comprises the steps of covering the surface of an electrically conductive support body with a thin insulation film, removing a portion of said insulation film, and forming a sensitive film of a metal oxide at least on the portion of the conductive support body where the insulation film was removed.

In still further aspect of this invention, a method of producing a pH measuring electrode is provided, which comprises the steps of forming a sensor film of a metal oxide on a portion of an electrically conductive support body, and thereafter covering the remaining portion of said support body with an insulation film.

For the conductive supporting body, any metals having conductivity such as aluminum, tantalum, platinum, titanium, iridium may be used. Also, for the insulation film deposited on the surface of the conductive support body, an insulation oxide such as alumina ($Al_2O_3$), tantalum pentoxide ($Ta_2O_5$), silicon dioxide ($SiO_2$) or the like, an insulation nitride such as silicon nitride ($Si_3N_4$) or the like, or a plastic material such as fluoroplastics or the like, may be used. Naturally oxidized films may be used as the insulation film, or they may be formed using such process as thin-film production technology like sputtering, CVD, etc., or heating oxidation, or dip coating using metal alkoxide as a material.

In various embodiments of the present invention which will be described hereinafter, iridium oxide is used as a sensitive film of a pH measuring electrode. This film is formed on the surface of an electrically conductive support body using thin-film production technology such as sputtering or ion beam deposition, and therefore a very small sensitive film can be obtained. Further, electrically conductive support bodies of any shapes such as a plate, rod, pipe or the like, can be used. Thus, a quite small pH measuring electrode can be constructed in comparison with prior electrodes. For example, a very small iridium oxide sensor film can be formed on a conductive support body in the form of a needle.

These and other objects, features and advantages of the present invention will become clear when reference is made to the following description of the preferred embodiments of the present invention, together with reference to the accompanying drawings.

BRIEF DESCRIPTION OF THE DRAWINGS

FIG. 1 is a sectional view showing a sensor section of a pH measuring electrode according to the present invention;

FIG. 2 is a partial sectional view showing the first embodiment of the pH measuring electrode of the present invention in which the sensor section shown in FIG. 1 is used;

DESCRIPTION OF THE PREFERRED EMBODIMENTS

Figure 3:
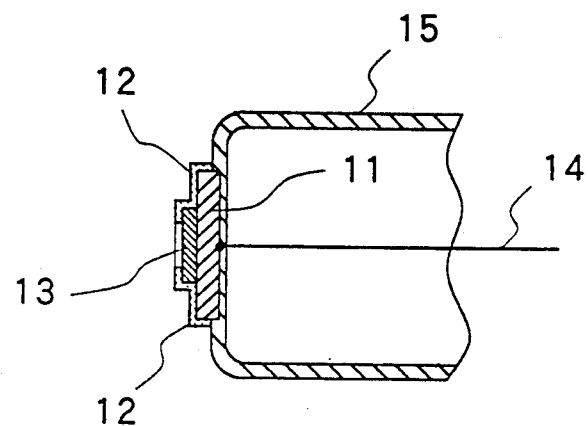
FIG. 3 is a sectional view showing a sensor section of a second pH measuring electrode according to the present invention.

Now, embodiments of the present invention will be described in detail with reference to the accompanying drawings.

FIG. 1 illustrates a sensor section of a first embodiment of the present invention. A thin insulation film 2 is formed on the surface of an electrically conductive support body 1 by conventional thin-film production technology such as natural oxidation, anode oxidation or deposition. Before the formation of an iridium oxide sensitive film 3, a portion of the insulation film 2 is removed. The iridium oxide sensitive film 3 is formed on the portion where this insulation film 2 is removed. The sensitive film 3 is electrically connected to the conductive support body 1 underlying it at the same time as the sensitive film 3 is formed. The insulation film 2 can be removed by various types of mechanical or chemical means. In particular, in case sputtering or ion beam deposition is used to form the iridium oxide sensitive film 3, a portion of the insulation film 2 can be removed by atoms striking it at high speeds. Therefore, the insulation film 2 can be removed easily, and the sensitive film 3 can be formed easily and minute working is possible.

FIG. 2 shows the first embodiment of the pH measuring electrode of the present invention in which the sensor section shown in FIG. 1 is used. A portion of the insulation film 2 on the end at one side of the conductive support body 1 opposite to the other side thereof on which the iridium oxide sensitive film 3 is formed is removed and a lead wire 4 is connected thereto, and thereafter, the conductive support body 1 at the end to which the lead wire 4 is connected, and the lead wire 4, are bonded in the form of a column in a supporting pipe 5 made of PVC, thus forming a pH measuring electrode.

Therefore, an electrode for measuring pH produced by a method of the present invention is formed in a state in which the iridium oxide sensitive film 3 is electrically connected to a predetermined position of the conductive support body 1. The surface of the conductive support body 1 other than the portion where the iridium oxide sensitive film 3 is formed is covered with the insulation film 2. Therefore, a lead wire to an electric potential difference detecting section can be taken out from the conductive support body 1.

As for iridium oxide sensitive films used in the present invention, it has been seen that excellent linear response is obtained in the range of pH of 0 to 14 and the response speed is high and stable for a long time. Therefore, the measurable range of pH is much wider and the stable period is long as compared with those of conventional pH measuring electrodes and ISFET electrodes in which sensitive films of metals such as platinum, or metal oxide such as titanium oxide are used. Also, in comparison with normal glass electrodes, the pH measuring electrode of this invention having the iridium oxide sensitive film is much stronger difficult to break, and has excellent resistance to chemicals since iridium oxide is used. As a result, it has an advantage that there is substantially no limitation on solutions to be measured.

Iridium oxide (in a hydrated state) and hydrogen ions are kept in an equilibrium state indicated by the following equation (1) in a water solution. Equilibrium electric potential at this time can be expressed by the following equation (2).

$$2IrO_2 + 2H^+ + 2e^- = Ir_2O_3 + H_2O \qquad (1)$$

$$E(mV) = 681 - 59.1\, pH\ (at\ 25°\ C.) \qquad (2)$$

That is, an asymmetrical electric potential is different from that of a glass electrode, but an electromotive force per pH is 59.15 mV/pH at 25° C. by Nernst equation.

If the ratio of 0 in iridium oxide to Ir goes out of the range of between 2.5 and 3.5, excellent response cannot be obtained and stability decreases. For example, Table 1 shows the relationship between the electric potential differences and immersion times, obtained for each electrode of the present invention in which the ratio of O of the iridium oxide to Ir was changed when the electrodes of the present invention were used as working or indicator electrodes and silver-silver chloride electrodes were used as reference electrodes and the electric potential differences were measured at regular intervals while both electrodes were immersed in a standard solution of pH 6.86. It can be seen that when the ratio of Ir:O is 1:3, a stable electric potential difference is obtained for a long period of time, whereas when the ratio of Ir:O is 1:2 or 1:4, the variations in the electric potential difference are quite large.

TABLE 1

| Immersion Time (hr) | Electric Potential (mV) Ir:O | | |
|---|---|---|---|
| | 1:3 | 1:2 | 1:4 |
| 0 | 251 | 278 | 185 |
| 50 | 246 | 232 | 94 |
| 150 | 245 | 196 | 62 |
| 400 | 246 | 181 | 89 |

The pH measuring electrode of the above-described first embodiment was produced in the following process. The tantalum pentoxide insulation film 2 having its thickness of 70 Å was formed by natural oxidation on the entire surface of the conductive support body 1 made of a tantalum wire having its diameter of 0.5 mm and its length of 2 cm. With a sensor film forming section of 0.2 mm ×3 mm left at one end of the conductive support body 1 covered with this insulation film 2, the remaining portion thereof was masked and then it was put into a film formation chamber of a sputtering apparatus and an Ir target was sputtered at a voltage of 0.8 KV for 100 minutes under an oxidizing atmosphere. At the sensor film forming section where the conductive support body 1 was exposed, the insulation film 2 thereon was almost completely removed and the iridium oxide sensor film 3 in which Ir:O is 1:3 was formed with its thickness of 1000 Å in such a manner that the sensor film 3 contacts with the conductive support body 1. After a portion of the insulation film 2 on the other side of the conductive support body 1 was removed and the lead wire 4 was connected thereto, the conductive support body 1 and the lead wire 4 are bonded in the form of a column in a supporting pipe 5 made of PVC, except the one side of the conductive support body 1 including the iridium oxide sensor film 3, and thus a pH measuring electrode was obtained.

The pH response of each of the pH measuring electrodes obtained was examined under such a condition that each electrode was used as an indicator electrode and a conventional calomel electrode was used as a reference electrode. The result showed that excellent linear response was obtained in the range of pH of 0 to 14 at a slope of 59.9 mV. Also, electric potential difference therebetween was measured by immersing them in standard solutions having pH of 1.68 and pH of 12.00 alternately, and as a result, excellent reproducibility shown in Table 2 was obtained.

TABLE 2

| pH of Standard Solution | Electric Potential (mV) |
|---|---|
| 1.68 | 552 |
| 12.00 | −66 |

TABLE 2-continued

| pH of Standard Solution | Electric Potential (mV) |
|---|---|
| 1.68 | 552 |
| 12.00 | −66.5 |
| 1.68 | 551.5 |
| 12.00 | −66 |

It should be noted that, in the above-described embodiment, the sensitive film 3 may be formed on a predetermined portion of the surface of the conductive support body 1 before the insulation film 2 is formed thereon, and thereafter, the insulation film 2 may be formed on the remaining portion of the surface of the conductive support body 1 by ordinary thin-film production technology such as natural oxidation or depositon.

FIG. 3 is a sectional view showing a sensor section of a second embodiment of the present invention. A platinum lead wire 14 is connected to a platinum disc 11 on which no insulation film is formed. This lead wire 14 is inserted into an aperture formed through the end face of a glass tube 15 thereby contacting the surface of the platinum disc 11 to which the lead wire 14 is connected with the end face of the glass tube 15. Thereafter, this assembly of the glass tube 15 and the platinum disc 11 is heated to fuse the platinum disc 11 to the end face of the glass tube 15. Then, an iridium oxide sensitive film 13 is formed on a portion of the surface (the surface where the lead wire 14 is not connected) of the platinum disc 11 and an insulation film 12 is formed on the remaining portion of the surface of the platinum disc 11 by ordinary thin-film production technology such as natural oxidation, anode oxidation or deposition. In this embodiment, this sensitive film 13 is also electrically connected to the platinum disc 11 underlying the film 13 at the same time as the sensitive film 13 is formed.

Figure 4:
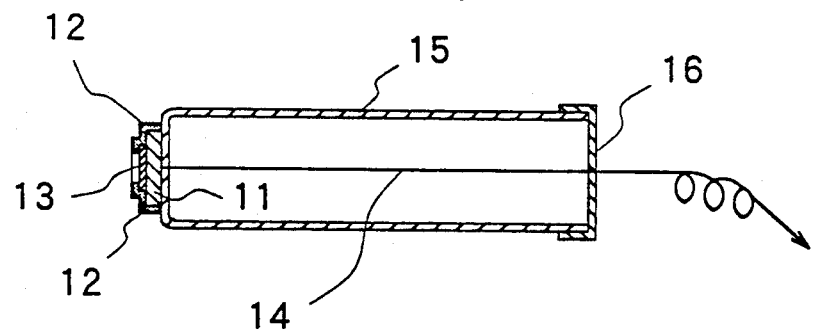
FIG. 4 is a sectional view showing the second embodiment of the pH measuring electrode of the present invention in which the sensor section shown in FIG. 3 is used.

FIG. 4 is a sectional view showing the second embodiment of the pH measuring electrode of the present invention in which the sensor section shown in FIG. 3 is used. This pH measuring electrode was produced in the following process. The surface of the platinum disc 11 having its diameter of 2 mm and its thickness of 0.2 mm to which the lead wire 14 was not connected was fused to the end face of the glass tube 15 in the above-described manner and an oxide film produced on the surface thereof was fully removed by acid washing. Thereafter, said surface of the platinum disc 11 was masked except a circular sensor film forming portion having its diameter of 1 mm at the center thereof. Then, it was put into a film formation chamber of a sputtering apparatus and an Ir target was sputtered at a voltage of 0.8 KV for 100 minutes under an oxidizing atmosphere. Next, the iridium oxide sensor film 13 formed on the platinum disc 11 was masked and immersed in an alkaline solution for 24 hours thereby forming the oxide film 12 on the entire exposed surface of the platinum disc 11 excluding the surface of the iridium oxide sensor film 13. That is, the entire exposed surface of the platinum disc 11 excluding the surface of the iridium oxide sensor film 13 was covered with the oxide film or insulation film 12.

The pH response of each of the pH measuring electrodes obtained was examined under such a condition that each electrode was used as an indicator electrode and a conventional calomel electrode was used as a reference electrode. The result showed that excellent linear response was obtained in the range of pH of 0 to 14 at a slope of 59.9 mV.

It should be also noted that, in this embodiment, after the entire exposed surface of the platinum disc 11 is covered with the insulation film 12, a predetermined portion of the insulation film 12 may be removed to form the iridium oxide sensor film 13 thereon in the same manner as in the first embodiment.

Figure 5:
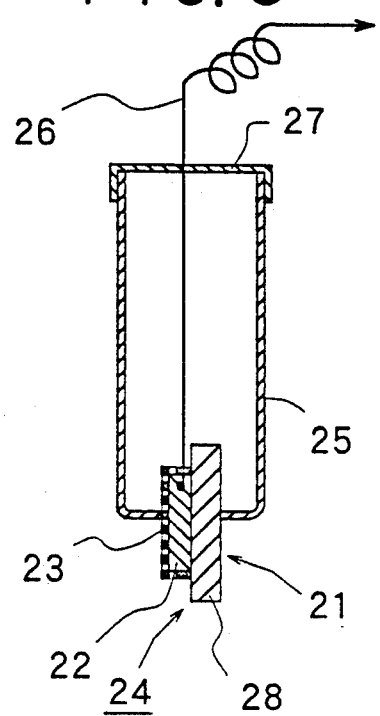
FIG. 5 is a sectional view showing a third pH measuring electrode according to the present invention.
Figure 6:
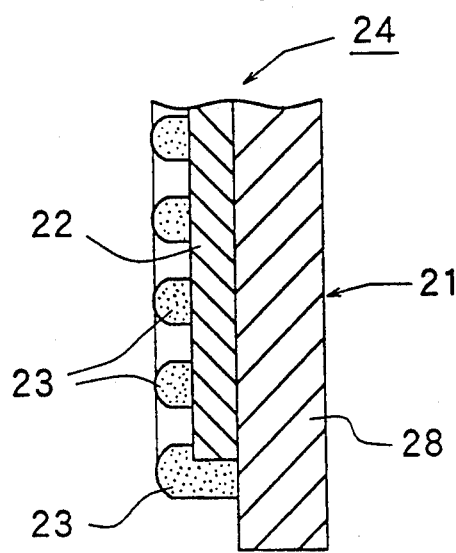
FIG. 6 is an enlarged sectional view showing the sensor section of the third pH measuring electrode shown in FIG. 5.

FIG. 5 shows a third embodiment of the pH measuring electrode according to the present invention, and FIG. 6 shows in enlarged sectional view the sensor section of the pH measuring electrode shown in FIG. 5. The pH measuring electrode of this embodiment includes a sensor section 24 comprising a sensor film support body 21 having a predetermined shape and dimension, a metal oxide film 22 formed on one surface of the support body 21 by, for example, sputtering, and a porous film 23 of an insulation material coated on the entire surface of the metal oxide film 22 by, for example, sputtering. This sensor section 24 is mounted in an aperture formed through the bottom face of a cylindrical supporting tube 25 in a watertight (liquid-tight) state. In this embodiment, about half of the metal oxide film 22 serving as a sensitive film is positioned outside of the supporting tube 25 and will be brought into contact with a solution pH of which is to be measured (a solution to be tested). An electrode lead-out wire 26 is electrically connected to an upper end section of the metal oxide film 22 positioned inside the supporting tube 25. This lead-out wire 26 passes within the supporting tube 25 into which no solution is leaked so that it reaches a cap 27 closing an upper end opening of the supporting tube 25 without contacting with any solution. The lead-out wire 26 passes through the cap 27 and then is connected to an input jack of a measuring circuit not shown.

The sensor film support body 21 functions as a support body for the metal oxide film 22, and in this embodiment, a plate-like body 28 of an insulating material made of a sapphire having its dimension of 5 mm × 5 mm and its thickness of 0.5 mm is used. However, insulating materials other than sapphire, for example, inorganic materials such as glass, ceramics or the like, or plastic materials such as polyvinyl chloride (PVC), fluoroplastics or the like may be used. The shape and dimension of the support body 21 may be selected at will. For example, support bodies of various shapes such as rod-like, cylindrical or square-cylindrical members may be used.

For the metal oxide film 22, a metal oxide such as iridium oxide, palladium oxide or titanium oxide may be used. The metal oxide film 22 is formed on the support body 21 using thin-film production technology such as sputtering or CVD. In this embodiment, an iridium oxide film having its dimension of 4 mm × 4 mm and its thickness of 1000 Å was formed on the supporting body 21 of sapphire by sputtering.

For the porous film 23 of an insulation material, inorganic insulating materials such as alumina ($Al_2O_3$), tantalum pentoxide ($Ta_2O_5$), silicon dioxide ($SiO_2$) or the like, or plastic materials such as fluoroplastics or the like may be used. The porous insulation film 23 is formed using thin-film production technology such as sputtering, CVD or the like, or dip coating using metal alkoxide as a raw material. The porous insulation film 23 acts to remove inhibition or interference on the pH sensor film by inhibiting substances and protects the pH sensor film. It is considered that the porous insulation film 23 serves to prevent the inhibition or interference by permitting only hydrogen ions to pass through its holes and not permitting any other ions to pass therethrough.

Therefore, the hole dimension of the porous film 23 must be larger than the diameter of hydrogen ions (in a hydrated state) of 2.8 Å in order for hydrogen ions to pass through the porous insulation film. On the other hand, if the hole diameter of the porous film 23 is too large, the sensor film is affected by an oxidizing or reducing agent, so the hole diameter thereof must be appropriately large. Since the smallest ion radius of oxidizing and reducing agents known to affect the sensor film at the present time is 8 Å (namely, 16 Å in diameter), if the hole diameter of the porous film 23 is 15 Å and less, the porous film can be formed which permits only hydrogen ions to pass therethrough and does not permit other ions to pass therethrough. Suitable diameter of the porous film can be found by changing film-forming conditions variously.

In this embodiment, silicon dioxide was deposited on the entire surface of the metal oxide film 22 by sputtering so that a porous insulation film 23 having a great number of holes through which hydrogen ions pass and other larger ions or compounds do not pass was formed. The porous film 23 will become a porous film or a non-porous film depending upon film-forming conditions. In the present invention, film-forming conditions are controlled so that a great number of holes which hydrogen ions pass and other larger ions or compounds do not pass are produced in the porous film formed during the process of forming the porous film 23. Of course, if the film-forming conditions are controlled so that the porous film formed has a great number of holes through which ions other than hydrogen ions pass, it is possible to use it as an ion measuring electrode. Although the porous film 23 was coated on the entire surface of the metal oxide film 22 in this embodiment, it is sufficient that the porous film 23 is coated on only the portion of the metal oxide film 22 which contacts with a solution pH of which is measured, i.e., only on the surface portion of the metal oxide film 22 which contacts a liquid, because the portion of the metal oxide film 22 positioned inside the supporting tube 25 does not function as a pH sensitive film. Also, the porous film 23 may be laminated on the metal oxide film 22 as a laminate of 2 to 4 layers of porous insulation films and each layer thereof may be made of a different insulation material from each other. Such construction is preferred since the upper layer of the laminate serves as a protective film for the underlying layer thereof and so the laminate has further improved resistances to wear and to chemicals and its function as the protective film for the sensor film is remarkably increased. In such case, the hole diameter of the lowest layer thereof is 3 Å or more and 15 Å and less, and the hole diameter of the remaining layer or layers thereof is larger than that of the immediate underlying layer thereof in order.

In the above-described third embodiment, a cylindrical glass tube is used as the supporting tube 25. However, the shape and material of the supporting tube may be changed at will. In short, any supporting body having a space within which an electrode lead-out wire can be housed may be used as the supporting tube. Needless to say, in case of measuring the pH of a hydrofluoric acid type solution, a supporting tube made of a material which is not corroded by hydrofluoric acid should be used.

Figure 7:
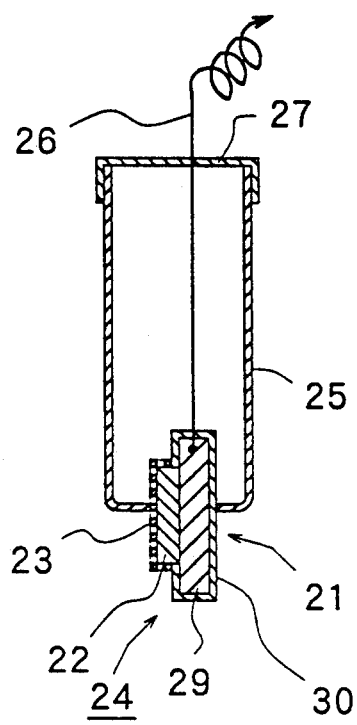
FIG. 7 is a sectional view showing a fourth pH measuring electrode according to the present invention.

FIG. 7 is a sectional view showing a fourth embodiment of the present invention. In this embodiment, a support body in which an insulating material 30 is coated on the entire surface of a metal plate 29 is used as the support body 21 supporting the metal oxide film 22 instead of using a support body made of an insulating material as in the above-described third embodiment, and the electrode lead-out wire 26 is connected to the metal plate 29. Since other construction thereof is the same as in the third embodiment, the explanation thereof is omitted and the components of this embodiment corresponding to those of the third embodiment are given the same reference numerals. Although there is no insulation film 30 between the metal oxide film 22 and the metal plate 29 in FIG. 7, the insulation film 30 has previously benn coated on the entire surface of the metal plate 29, and then a portion of the insulation film 30 therebetween is removed by, for example, sputtering the metal oxide film 22 to said portion of the insulation film 30 and the metal oxide film 22 is securely connected to the metal plate 29. Therefore, it is not necessary that the insulation material on which the metal oxide film 22 is deposited is removed beforehand from the metal plate 29. Since the electrode lead-out wire 26 can be connected to the metal plate 29 in this embodiment, there are advantages that the connection of the lead-out wire 26 to the metal plate 29 is firm and a working of the connection is easy and the like.

For the metal plate 29, any electrically conductive metals such as aluminum, tantalum, platinum, titanium, iridium or the like may be used. For the insulating material 30 coated on the entire surface of the metal plate 29, insulation oxides and nitrides such as alumina ($Al_2O_3$), tantalum pentoxide ($Ta_2O_5$), silicon dioxide ($SiO_2$), silicon nitride ($Si_3O_4$) or the like, or plastic materials such as fluoroplastics or the like may be used. A naturally oxided film may be used as the insulation film 30, or it may be formed using a manufacturing method such as thin-film production technology as sputtering, CVD or the like, heating oxidation, or dip coating using metal alkoxide as a raw material. In this embodiment, tantalum was used as the metal plate 29, and as the insulation film 30 was used tantalum pentoxide formed on the entire surface of this tantalum plate by natural oxidation. Also, the metal oxide film 22 coated on the metal plate 29 was formed by sputtering iridium oxide, and the porous insulation film 23 was formed on the metal oxide film 22 by sputtering tantalum pentoxide.

Figure 8:
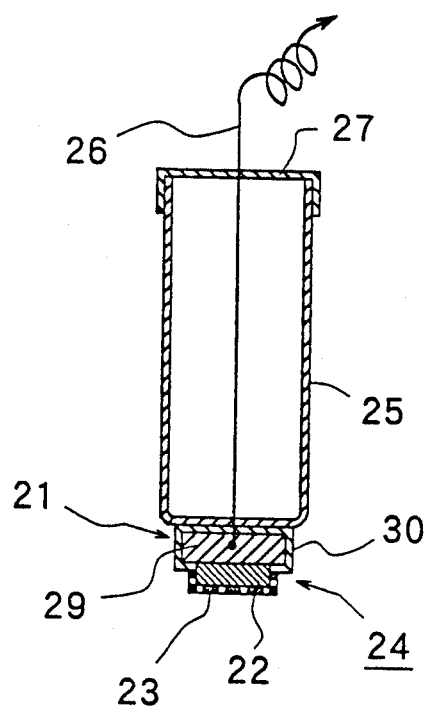
FIG. 8 is a sectional view showing a fifth embodiment of the present invention which is a modification of the fourth embodiment of the present invention shown in FIG. 7.

FIG. 8 is a sectional view showing a fifth embodiment of the present invention, which is a modification of the fourth embodiment of the present invention shown in FIG. 7. In this embodiment, the sensor section 24 shown in FIG. 7 is mounted on the bottom surface of the cylindrical supporting tube 25. In this case, it is only necessary to provide an aperture through which only the electrode lead-out wire 26 passes through the bottom surface of the supporting tube 25. Since other construction thereof is the same as in the third embodiment, the explanation thereof is omitted and the components of this embodiment corresponding to those of the third embodiment are given the same reference numerals.

In this manner, in case the electrode lead-out wire 26 can be connected to the metal plate 29 of the supporting body 21, there is an advantage that a working for mounting the sensor section 24 becomes quite easy, because it is not necessary to house a portion of the sensor section 24 inside the supporting tube 25.

As a typical example, in the pH measuring electrode constructed as shown in FIG. 8, a tantalum disc having its thickness of 0.5 mm and its diameter of 4 mm was used as the metal plate 29 and the film of tantalum pentoxide formed on the entire surface of this tantalum disc by natural oxidation was used as the insulation film 30. A circular iridium oxide film having its diameter of 3 mm was deposited on the tantalum disc having said insulation film of tantalum pentoxide by sputtering through a masking material covering a predetermined portion of the tantalum disc thereby forming a pH sensitive film of approximately 1000 Å in thickness. Thereafter, the masking material was removed and the porous insulation film 23 of tantalum pentoxide was deposited in thickness of 500 Å on the entire surface of the iridium oxide film by sputtering thereby constructing the sensor section 24. This sensor section 24 was fixed to the bottom surface of the supporting tube 25 of cylindrical glass, as shown in FIG. 8.

For the pH measuring electrode of this invention constructed as described above, the function and effect of the porous insulation film 23 having its hole diameter of 10 Å was examined using L-ascorbic acid solution as a typical example of oxidizing and reducing agents. The test was carried out using said pH measuring electrode of this invention and in addition thereto, a glass electrode, a pH measuring electrode having an iridium oxide sensor film coated with a porous insulation film of 20 Å or more in its hole diameter, and a pH measuring electrode having no porous insulation film coated on the iridium oxide sensor film, that is, having the iridium oxide sensor film exposed, for comparison. After these four electrodes were calibrated by immersing them in two pH standard solutions of pH 6.86 and pH 4.01 in proper sequence, the electric potential differences thereof in L-ascorbic acid solution were measured, respectively and were converted into pH to evaluate them. When the concentration of the L-ascorbic acid was $1 \times 10^{-2}$ mol/l, the pH measuring electrode having the iridium oxide sensor film exposed and the pH measuring electrode having iridium oxide sensor film with a porous insulation film of 20 Å both responded at one second or less for both the standard solutions of pH 6.86 and pH 4.01 and showed Nernstian slope of 58.6 mV/pH for both standard solutions, respectively. However, the electric potentials obtained from said both electrodes were lack of stability when they immersed in L-ascorbic acid solution and tended to drift in one direction. On the contrary, in case of the pH measuring electrode of the present invention having the iridium oxide sensor film coated with the porous film of 10 Å in its hole diameter and the glass electrode, stable electric potentials were immediately obtained therefrom respectively when they were immersed in both the standard solutions as well as in the L-ascorbic acid solution. Moreover, the electric potentials obtained therefrom were constant even after ten minutes elapsed. The results of the test are shown in Table 3. Further, above-mentioned measurement of electric potential differences was done using saturated KCl-silver/silver chloride electrode as a reference electrode.

TABLE 3

| Types of pH Measuring Electrodes | Electric Potential for pH Standard Solutions (mV) | | Nernstian Slope mV/pH | L-Ascorbic Acid $1 \times 10^{-2}$ mol/l | |
|---|---|---|---|---|---|
| | pH 6.86 | pH 4.01 | | Electric Potential (mV) | pH |
| Glass | 11 | 178 | 58.6 | 31 | 6.51 |
| Iridium Oxide with Porous Film of Hole Diameter of 10Å | 256 | 423 | 58.6 | 277 | 6.50 |
| Iridium Oxide with Porous Film of Hole Diameter of 20Å | 255 | 422 | 58.6 | Unstable | — |
| Iridium Oxide (No Protective Film) | 255 | 422 | 58.6 | Unstable | — |

As is clear from above Table 3, the pH measuring electrode of the present invention having the iridium oxide sensor film coated with the porous insulation film 23 has merely a difference of 0.01 pH in comparison with that of the glass electrode in the L-ascorbic acid solution, and it was seen that the pH measuring electrode of the present invention can measure pH of the L-ascorbic acid solution substantially without being affected by ascorbic acid. In other words, it was found that the pH measuring electrode of this invention can take accurate measurements equivalent to those of the glass electrode without being affected by coexistent substances.

Figure 9:
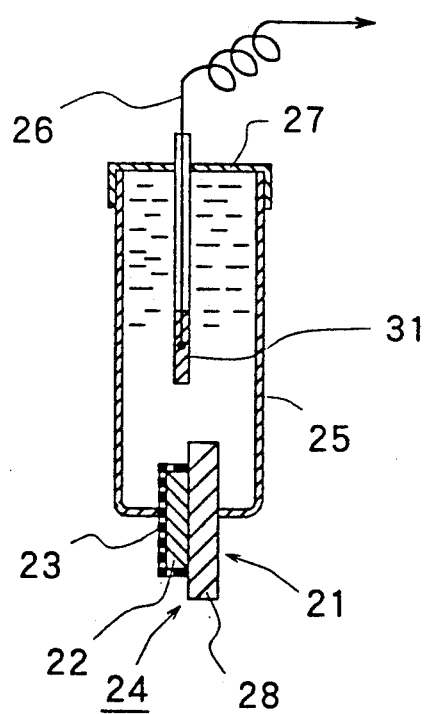
FIG. 9 is a sectional view showing a sixth pH measuring electrode according to the present invention.

FIG. 9 is a sectional view showing a sixth embodiment of a pH measuring electrode of the present invention. In this embodiment, the sensor section 24 of the pH measuring electrode has the same construction as that of the third embodiment shown in FIG. 5 but the electrode lead-out wire 26 is not connected to the metal oxide film 22 of the sensor section 24. Instead, a solution of a known pH is injected into the supporting tube 25 and an internal electrode 31 of normal construction is immersed in this solution. The electrode lead-out wire 26 is taken out from this internal electrode 31 so that an electric potential detected by sensor section 24 is outputted through the internal electrode 31.

In casee an electric potential detected by the sensor section 24 is outputted through the internal electrode 31, there is an advantage that the accuracy in measurement of pH is further improved because the reference electrode usually has an internal electrode and so both reference and pH measuring electrodes are well balanced with each other. Of course, the same effects can also be obtained from the pH measuring electrode of this embodiment in which the sensor section 24 thereof is substituted by a sensor section having the same construction as in the fourth embodiment shown in FIG. 7. Also, for the internal electrode 31, an electrode having the same construction as that of the sensor section 24 shown in FIG. 5, 7 or 8 may be used. Needless to say, in this case, the electrode lead-out wire 26 is taken out to the outside of the supporting tube 25 in such a manner that it does not contact with the solution within the supporting tube 25. When said electrode like the sensor section 24 is used as the internal electrode, the porous insulation film 23 covering the metal oxide film 22 is not always necessary.

In each embodiment of this invention mentioned above, iridium oxide was used as a metal oxide which functions as a sensor film, but the same function and effect as obtained from each embodiment can also be expected when using an oxide of a metal selected from Pd, Pt, Sn, Rh, Ta, Os, Ru, W and Ti having properties similar to Ir. Further, the construction and configuration of the sensor section and supporting tube, materials and substances to be used, methods of forming metal oxides or porous insulation films, and the like are not limited to those of the embodiments shown and described above.

As has been explained above, according to the present invention, since a sensitive film of a metal oxide is formed or deposited on an electrically conductive support body, the sensitive film can be very miniaturized in its size or dimension. Therefore, the entire pH measuring electrode can be made considerably small and simple in construction thereby accommodating the demand for smaller pH meters as well as making possible pH measurements in a special field of technology which requires very small electrodes.

The pH measuring electrode of this invention using a metal oxide sensor film is durable, has excellent resistance to chemicals, has a wide measurable range of pH of 0 to 14, has a high speed response characteristic of about one second, and has a stable response for a long period of time.

In addition, according to this invention, there can be provided a pH measuring electrode having its sensor film of a metal oxide which is not affected by any coexistent substances and has the same accuracy of measurement as that of a glass electrode by covering the entire surface of at least the portion of said sensor film contacting with a solution to be measured with a porous film of an insulation material, and therefore, the pH measuring electrode of this invention can be used not only in a field of technology in which glass electrodes are used but also in a field of technology in which glass electrodes cannot be used, for example, in a measurement of pH of hydrofluoric acid type solutions. Also, because the sensor film is covered with a porous insulation film, there is an effect that this porous film functions as a protective film for the sensor film. For example, though the surface of the electrode of this invention was violently rubbed with, for example, "Kimwipe" (trade name), the rubbing did not affect the characteristics of the sensor film of the electrode. Further, the pH measuring electrode having a metal oxide as its sensor film according to this invention has many features that it responds at high speed even after it was preserved in the atmosphere for a long time, is not affected by noises since it has a low electric resistance (internal resistance) as several KΩ (5 to 10KΩ), responds at high speed even after it was preserved in saturated KCl solution, does not crack or break because it has a considerable mechanical strength, can be miniaturized (e.g., a needle type pH measuring electrode can be formed), has no need of skillfull technique in production thereof, has no alkaline error, has the same wide measurable range of pH of 0 to 14 as that of a glass electrode, can be used at temperature range of 0° to 100° C. equivalent to that of a glas electrode, etc., and therefore there are remarkable effects that the pH measuring electrode of this invention can be used in a new field of technology which is in need of above-mentioned features thereof, etc.

Various modifications and changes of the embodiments of the present invention shown and described above may be made by those skilled in the art without departing from the spirit and scope of this invention. Therefore, it should be understood that the present invention is not limited to the specific embodiments described and shown in the specification and drawings, and is only limited in the appended claims.

What is claimed is:

1. a pH measuring electrode comprising:
   an electrically conductive metal substrate;
   an electrically insulative film covering a part of a surface of said metal substrate;
   a pH sensitive film comprising iridium oxide contacting said metal substrate so as to be electrically connected thereto, the ratio of iridium to oxygen in said iridium oxide being from 1:2.5 to 1:3.5;
   a porous insulation film deposited on at least the portion of the outer surface of the iridium oxide film where the iridium oxide film is to contact a solution whose pH is to be measured, said porous film having pores with a diameter of 3 Å to 15 Å so that only hydrogen ions, and no other ions, are permitted to pass through said porous film; and
   a lead-out conductor connected to said metal substrate.

2. An electrode according to claim 1 wherein said metal substrate is selected from the group consisting of tantalum and aluminum.

3. An electrode according to claim 1 wherein said electrically insulative film is selected from the group consisting of alumina and tantalum pentoxide.

4. An electrode according to claim 1 wherein said porous insulation film is selected from the group consisting of alumina, tantalum pentoxide and silicon dioxide.

5. An electrode according to claim 1 wherein said electrically insulative film is formed on said substrate by natural oxidation of said metal.

6. An electrode according to claim 1 wherein said porous insulation film is deposited on said iridium oxide film by sputtering.

7. An electrode according to claim 1 wherein said porous insulation film comprises a laminate of two to four layers successively coated on said iridium oxide film, the pore diameter of the layer closest to said iridium oxide film being 3 Å to 15 Å and the pore diameter of each successive layer of said laminate being larger than the pore diameter of said closest layer.

8. An electrode according to claim 1 wherein the part of the surface of said metal substrate covered with said electrically insulative film is subjected to sputtering from an iridium target under an oxidizing atmosphere, whereby the electrically insulative film is almost completely removed from said part of said metal substrate in such a manner as to effect the electrical connection of the pH-sensitive film to said metal substrate.

9. A pH electrode comprising:
   an electrically conductive metal substrate comprising tantalum and having an electrically insulative film comprising tantalum pentoxide on a portion of a surface of said substrate;
   a pH sensitive film comprising iridium oxide directly on said metal substrate so as to be electrically connected thereto, the ratio of iridium to oxygen of said iridium oxide being from 1:2.5 to 1:3.5;
   a porous insulation film of tantalum pentoxide directly deposited on the outer surface of said iridium oxide film by sputtering, said porous insulation film having pores, the diameter of each of which is between 3 Å and 15 Å so that only hydrogen ions are permitted to pass through the pores and other ions are not permitted to pass therethrough; and
   a lead-out conductor connected to said metal substrate.

10. A pH measuring electrode according to claim 9 further comprising a protective insulation film deposited on said porous insulation film, wherein said protective insulation film has pores the diameters of which are larger than the pore diameters of said porous insulation film.

* * * * *